United States Patent [19]

Samples

[11] Patent Number: 5,306,241
[45] Date of Patent: Apr. 26, 1994

[54] METHOD OF CATHETERIZATION ON AND BLADDER DRAINAGE

[76] Inventor: Charles R. Samples, 465 Barr Ct., Akron, Ohio 44319

[21] Appl. No.: 807,257

[22] Filed: Dec. 13, 1991

Related U.S. Application Data

[60] Division of Ser. No. 654,525, Feb. 13, 1991, Pat. No. 5,096,454, which is a continuation-in-part of Ser. No. 568,203, Aug. 16, 1990, abandoned.

[51] Int. Cl.⁵ ............... A61M 31/00; A61M 29/00; A61M 5/00; A61F 5/44
[52] U.S. Cl. ............................... 604/54; 604/96; 604/171; 604/352
[58] Field of Search ............... 604/49, 54, 55, 96–103, 604/171–175, 276, 278, 349, 351–353; 600/29–32; 128/DIG. 25

[56] References Cited

U.S. PATENT DOCUMENTS

| | | | |
|---|---|---|---|
| 3,606,889 | 9/1971 | Arblaster | 604/171 |
| 3,630,206 | 12/1971 | Gingold | 604/102 |
| 3,659,611 | 5/1972 | Miller | 128/207.15 |
| 3,769,981 | 11/1973 | McWhorter | 604/96 |
| 3,854,483 | 12/1974 | Powers | 604/172 |
| 3,894,540 | 7/1975 | Bonner, Jr. | 604/171 |
| 3,954,110 | 5/1976 | Hutchison | 604/102 |
| 4,062,363 | 12/1977 | Bonner, Jr. | 604/171 |
| 4,551,137 | 11/1985 | Osborne | 604/171 |
| 4,652,259 | 3/1987 | O'Neil | 604/54 |
| 4,716,896 | 1/1988 | Ackerman | 128/200.26 |
| 4,865,586 | 9/1989 | Halberg | 604/93 |
| 4,892,095 | 1/1990 | Nakhgevany | 128/207.14 |
| 4,986,810 | 1/1991 | Semrad | 604/106 |
| 5,149,326 | 9/1992 | Woodgrift et al. | 604/163 |

FOREIGN PATENT DOCUMENTS 2847455  5/1979  Fed. Rep. of Germany ...... 604/171

*Primary Examiner*—John D. Yasko
*Assistant Examiner*—Adam J. Cermak
*Attorney, Agent, or Firm*—Reising, Ethington, Barnard, Perry & Milton

[57] ABSTRACT

A catheter assembly for collecting fluid from a tubular organ into a drainage system includes a tubular body portion (12) having an end portion (14) and an intermediate portion (16) adjacent thereto. The end portion (14) includes a retaining balloon (30) for retaining the intermediate portion (16) within the tubular organ. The intermediate portion (16) includes a portion having an outer diameter smaller than the inner diameter of the catheterized tubular organ for allowing the free flow of fluid from the tubular organ and over the intermediate portion (16) to maintain the tubular organ infection free. A collection mechanism is operatively connected to the intermediate portion (16) and spaced from the end portion (14). The collection mechanism is insertable into the tubular organ for collecting the fluid flowing over the intermediate portion (16) and preventing fluid from escaping from the drainage system. A method of using the catheter assembly (10) is also disclosed.

16 Claims, 4 Drawing Sheets

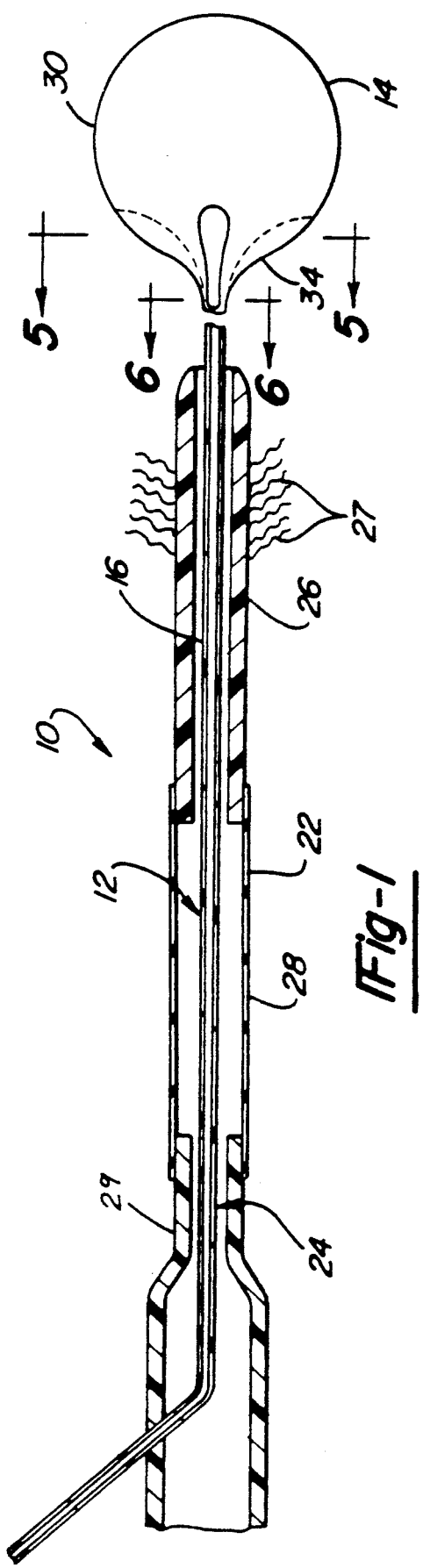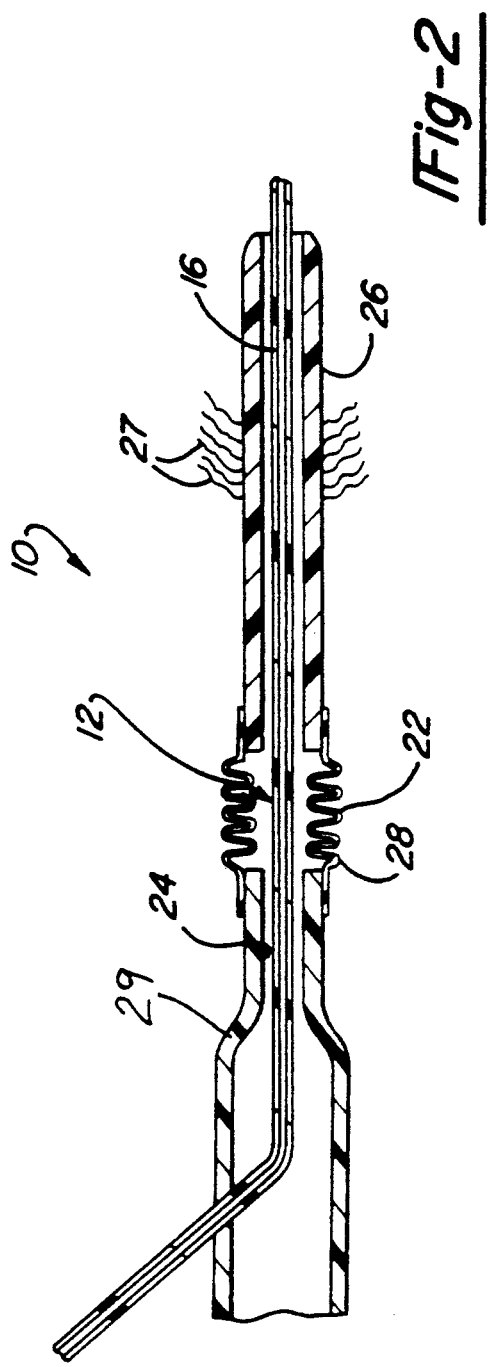

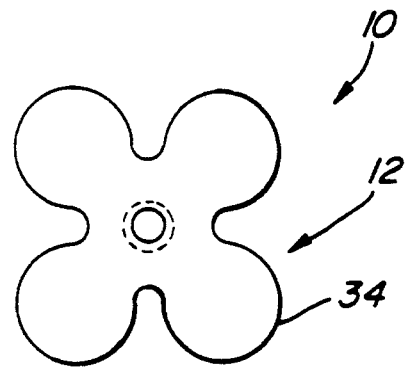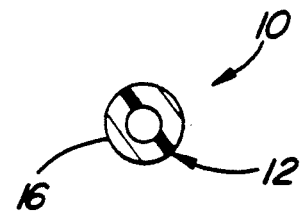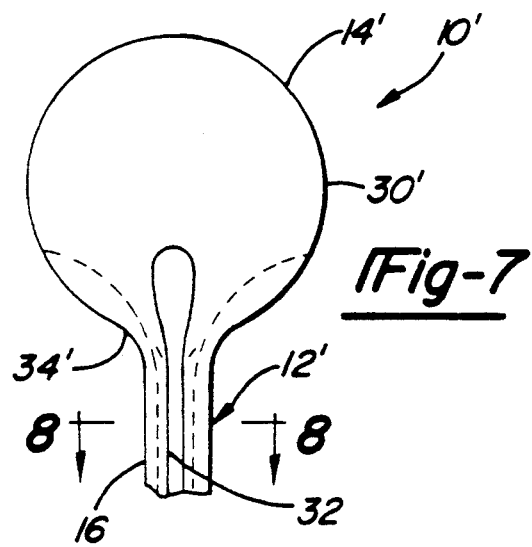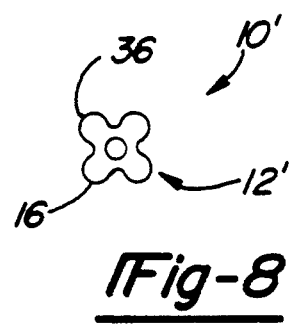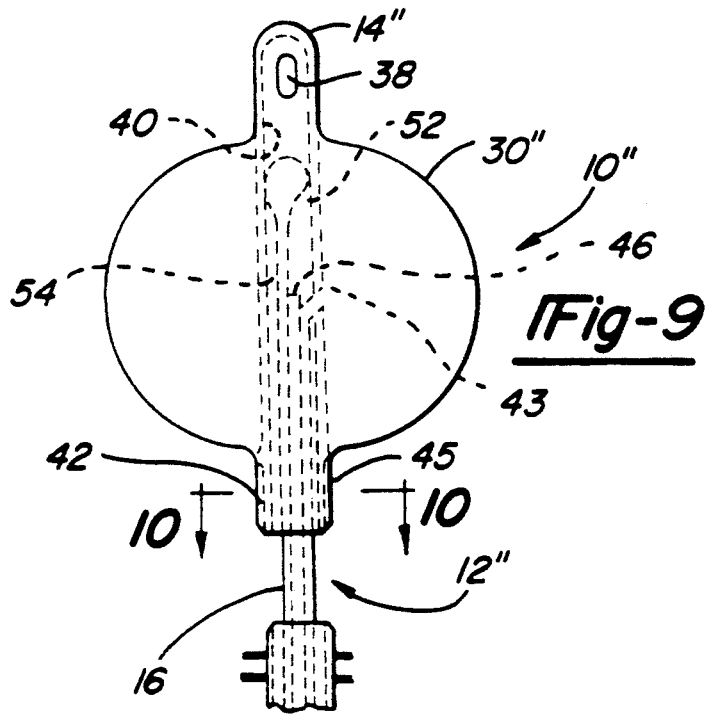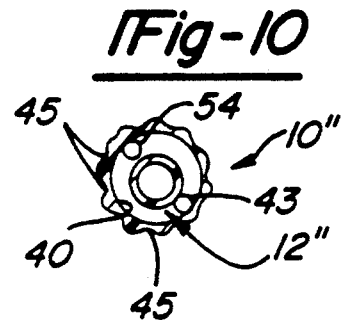

METHOD OF CATHETERIZATION ON AND BLADDER DRAINAGE

This is a division, of application Ser. No. 07/654,525, filed on Feb. 13, 1991, now U.S. Pat. No. 5,096,454 which is a continuation-in-part of Ser. No. 07/568,203 filed Aug. 16, 1990, now abandoned.

TECHNICAL FIELD

The present invention relates generally to the provision of a catheter assembly in the form of tubing having utility for medical devices and particularly urethral catheters. Such catheters are normally used as indwelling catheters that are placed and retained within the urethra and extend into the bladder for an extended period of time.

BACKGROUND OF THE INVENTION

Catheterization is required in post operative patients either to assist monitoring of the urine output or because they cannot release the sphincter muscle which has been traumatized by shock of an operation. Long term indwelling catheters are required by paraplegic patients whom have no control over their bladder. At least 50% of long term care residents in nursing homes are identified as incontinent and the problem is frequently managed with indwelling catheters.

Most paraplegic patients develope chronic bladder and kidney infections, and in the end succumb to infection or toxins produced by the infection which cause failure of other organs. Therefore, many paraplegics die from an infection which starts in the urethra or bladder as a result of infections introduced by the use of the catheter.

Urine and other body fluids excreted through the urethra are mediums in which a number of organisms can flourish. Therefore, even when the most sterile techniques are employed during the insertion of a catheter, there is still a path through which infectious organisms can enter the body, that being through the inside of the catheter directly into the bladder.

Yet another path by which infectious organisms can enter the body is along the outside surface of the catheter. Although sterile techniques may temporarily eliminate this path during catheter insertion, it is possible for such organisms to migrate along the outside of the catheter when the antiseptic effect of such techniques has worn off.

Bacterial sepsis can generally be treated successfully with antibiotics, but a complete treatment regimen can be expensive and time consuming. In addition, antibiotic therapy is often complicated by superinfections and increasingly, the appearance of antibiotic-resistant pathogenic strains. Mycotic infections (fungi, molds, yeasts), typically occasioned by extremely high fevers, are usually refractory to commonly employed antibiotics and as a result are often fatal.

One of the largest problems and the greatest dangers to the patient that exist when using an indwelling urethral catheter, such as a Foley catheter, is infection that occurs after the catheter has been indwelling for a few days. Clinical studies have shown that the catheter, both internally and externally, provides an avenue for entry of pathogenic organisms. In the former instance, with respect to organisms gaining access through the interior of the catheter, it is commonplace to provide means for killing organisms that would otherwise multiply in a urine drainage bag operatively connected to the catheter. In the latter instance, attempts have been made to prevent organisms from entering the urethral passage between the wall of the urethra and the exterior surface of the catheter. However, such attempts with respect to providing a barrier that would prevent organisms from entering the urethral passage between the urethra and catheter can result in introducing additional problems not the least of which is increased irritation and inflammation of tissue by prior art catheters, which condition materially enhances the likelihood of infection attendant the use of an indwelling catheter or the like. An indwelling catheter, such as a Foley catheter, is merely an example and the same problem exists with respect to other drainage tubes as well as venous catheters.

Generally, the attempts of the prior art to provide catheters intended to eliminate or minimize infection comprise catheters in which a microbiocide capable of withstanding the conditions attendant the manufacture of the catheter are actually incorporated in a composition comprising the catheter. Such catheters normally achieve a microbiocidal effect by virtue of the fact that in use the microbiocidal agents in the base material bleed to the surface. In the case of urethral catheters this results in irritation of the wall of the urethra. It is believed that catheters with such a construction are no longer in use.

A subsequent generation of indwelling catheters resorted to a somewhat different approach in an attempt to reduce infection. In this regard, and since the tubular body portion of most catheters is formed of a natural or synthetic elastomer that is hydrophobic, prior art catheters such as those formed of silicone rubber have had substantially their entire surfaces, both interior and exterior, coated with a hydrophillic polymer to enable the absorption of aqueous solutions of suspensions of microbiocide, including antibiotics into the coating.

In this regard U.S. Pat. No. 4,055,682 to Merril is directed to a catheter having a silicone body portion rendered hydrophilic by contacting it with N-vinyl pyrrolidone (NVP) and exposing the catheter and NVP to ionizing radiation. U.S. Pat. Nos. 3,566,874 and 3,695,921 to Shepherd et al are representative of indwelling Foley urethral catheters made of natural or synthetic rubber and having an external coating of a hydrophillic acrylate or methacylate polymer grafted thereto for reducing irritation and infection. The hydrophillic polymer may be impregnated with an antibiotic or germicide.

There are several problems encountered by the systems of Merril and Shepherd et al in that if a microbiocide is applied to substantially the entire surface of a catheter, in use it will cause irritation and probably do more damage to the patent than if a standard untreated catheter were used. Further, if an antibiotic is impregnated in the surface of a catheter then only those organisms that are rendered dormant or killed by the particular antibiotic would be effected. The protective flora would be damaged with a possibility that other organisms normally subdued by the flora would run rampant. Thus the use of an antibiotic impregnated catheter could tend to induce rather than prevent infection.

Rendering a surface of a catheter hydrophillic causes other problems. One of the most significant problems in this regard is brought about by the very nature of the coatings, its hydrophillicity, that provides a wettable surface. Once such a wettable surface is in contact with a physiological fluid such as urine, for example, which has dissolved salts and other solid compounds in its composition, the hydrophillic coating, by virtue of uptake of the aqueous moiety of such physiological fluid, provides a nucleus for the accretion of salt due to a supersaturated condition adjacent the coating as well as accretion of other solid components of the composition. An unfortunate end result is a plugged catheter or a catheter with a sharp accretion of salts and the like on the exterior surface of the catheter. Needless to say, in the instance of an urethral catheter having such an accretion on the exterior thereof, the removal of the catheter brings about a situation not unlike the passing of a jagged kidney stone through the urethra.

The U.S. Pat. No. 4,878,901 to Sachse, issued Nov. 7, 1989 discloses an indwelling urethral catheter arrangement for the prevention of ascending bacterial infection which flushes downwardly the bacteria by urine permitted to flow along the inside of the urethral wall, the entire urinary stream being conducted with aid of a condom like sheath fittable over the tip of the penis to the outside of the catheter arrangement. The condom is necessary to prevent soiling of the patient's clothing. This arrangement is only suitable for male patients and further requires the uncomfortable situation of the continual need for the condom-like sheath.

The present invention provides a catheter assembly which is maintained completely within the urethra and includes means which prevent leakage without requiring an external fluid catch, such as a condom like member.

SUMMARY OF THE INVENTION

In accordance with the present invention, there is provided a catheter for collecting fluid from a tubular organ into a drainage system, the catheter including a tubular body portion having an end portion and an intermediate portion adjacent thereto. The end portion includes retaining means for retaining the intermediate portion within the tubular organ. The intermediate portion includes flow means for allowing the free flow of fluid from the tubular organ and over the intermediate portion and the tubular organ to maintain an infection free tubular organ. Collection means is operatively connected about the intermediate portion and spaced from the end portion. The collection means is insertable into the tubular organ for collecting the fluid flowing over the intermediate portion and preventing the fluid from escaping from the drainage system.

The present invention further provides a method for collecting fluid from the tubular organ and into the drainage system. The method includes the steps of inserting a tubular body portion having an end portion and an intermediate portion adjacent thereto into the tubular organ, retaining the intermediate portion in the tubular organ, inserting a plug end portion of a collection mechanism of the second tubular member disposed over the intermediate portion into the tubular organ and allowing the free flow of urine from the tubular organ and over the intermediate portion maintaining an infection free tubular organ. The fluid flowing over the intermediate portion is collected into the collection mechanism while preventing the escape of the fluid from the drainage system.

FIGURES IN THE DRAWINGS

Other advantages of the present invention will be readily appreciated as the same becomes better understood by reference to the following detailed description when considered in connection with the accompanying drawings wherein:

FIG. 1 is a cross sectional view of the present invention;

FIG. 2 is a cross sectional view of the present invention wherein a portion is collapsed;

FIG. 5 is a cross sectional view taken substantially along lines 5—5 of FIG. 1;

FIG. 6 is a cross sectional view taken substantially along lines 6—6 of FIG. 1;

FIG. 7 is a cross sectional view of a second embodiment of the inflatable portion of the present invention;

FIG. 8 is a cross sectional view taken substantially along lines 8—8 of the FIG. 7;

FIG. 9 is a cross sectional view of third embodiment of the inflatable portion of the present invention;

FIG. 10 is a cross sectional view taken substantially along lines 10—10 of FIG. 9.

DETAILED DESCRIPTION OF THE INVENTION

Figure 3:
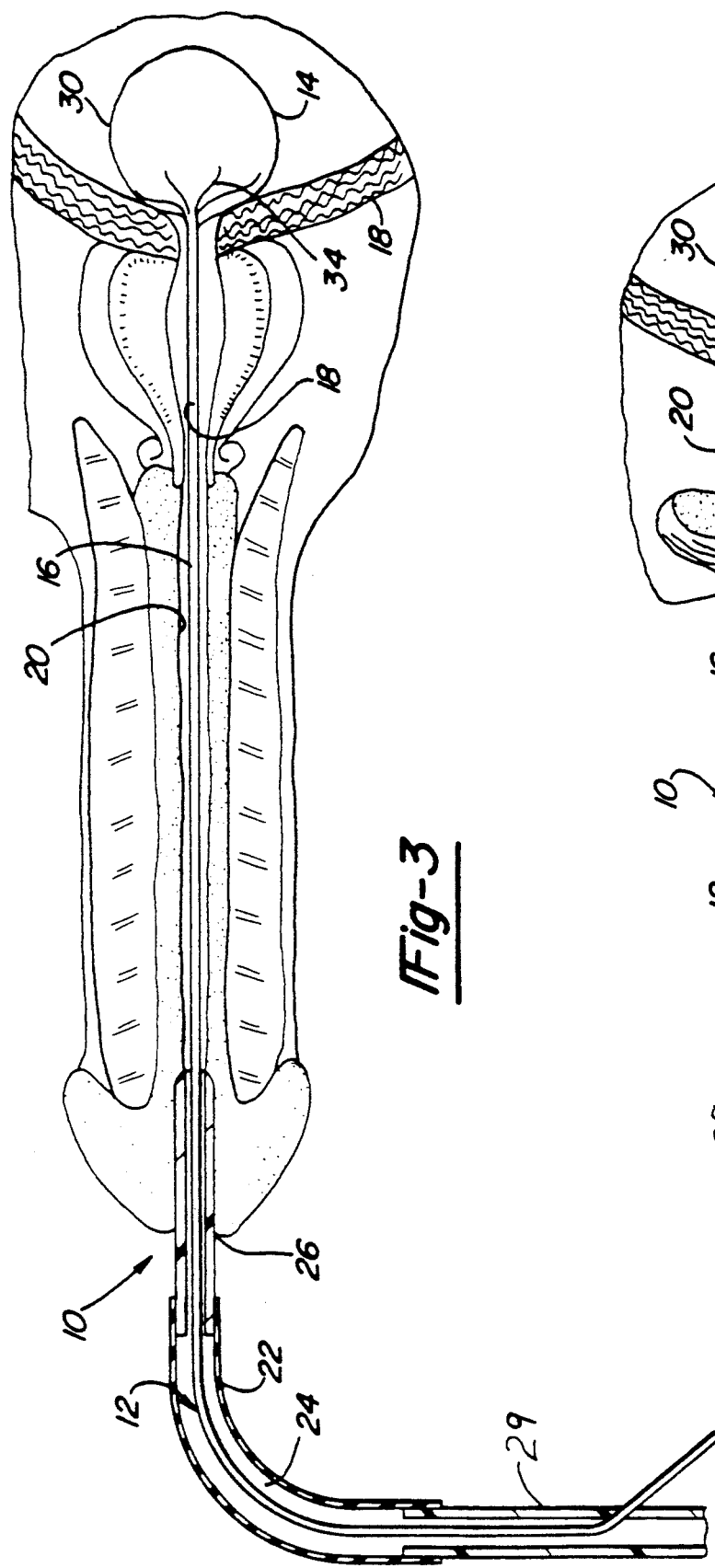
FIG. 3 is a cross sectional view of the present invention used to catheterize a male.

A catheter for collecting fluid from a tubular organ into a drainage system is generally shown at 10 in the drawings. Primed numbers are used to indicate like structures between the several embodiments.

Such catheterizations are intended to include intervenous, peritoneal dialysis, parenteral and urological catheters as well as vascular graphs, ventricular and peritoneovenous shunts, penile prostheses and other catheterizations. This list is not intended to be complete but rather an example of such uses.

As a catheter, or as a prostheses, the present invention can be used in any situation wherein the flow through an artery, vein, lumen, cavity of the tubular organ, or along the surface of an organ or body part wherein the application or installation of a catheter or prosthetic device may cause bacteria or fungi to grow, propagate, colonize, migrate and cause infection.

The present invention generally includes a tubular body portion 12. The tubular body portion 12 has an end portion 14 and an elongated intermediate portion 16 adjacent thereto. The end portion 14 includes retaining means for retaining the intermediate portion 16 within the tubular organ. The invention is characterized by the intermediate portion 16 including flow means for allowing the free flow of fluid from the tubular organ and over the intermediate portion 16 and tubular organ to maintain an infection free tubular organ and collection means operatively connected about the intermediate portion 16 and spaced from the end portion 14, the collection means being insertable into the tubular organ for collecting the fluid flowing over the intermediate portion and preventing the fluid from escaping from the drainage system. Thus, the present invention allows the circulation and flow of body fluids to maintain the area about the intermediate portion 16 free from infection and collects the fluid within the tubular organ.

The present invention utilizes the fact that in a normally functioning urinary track, the periodic flow of urine through the urethra prevents bacteria or fungi from multiplying and migrating and does not allow incrustations and urethral strictures to form. The present invention provides a catheter structure and method of use that substantially overcomes the problems of the prior art indwelling catheters by utilizing this concept of bodily fluid flow to prevent infection. With regard to the urinary tract, the present invention prevents urinary tract infection by utilizing the periodic flow of urine to clean the urethra and prevent the multiplying and migration of bacteria and fungi and the formation of incrustation and urethral strictures.

Figure 4:
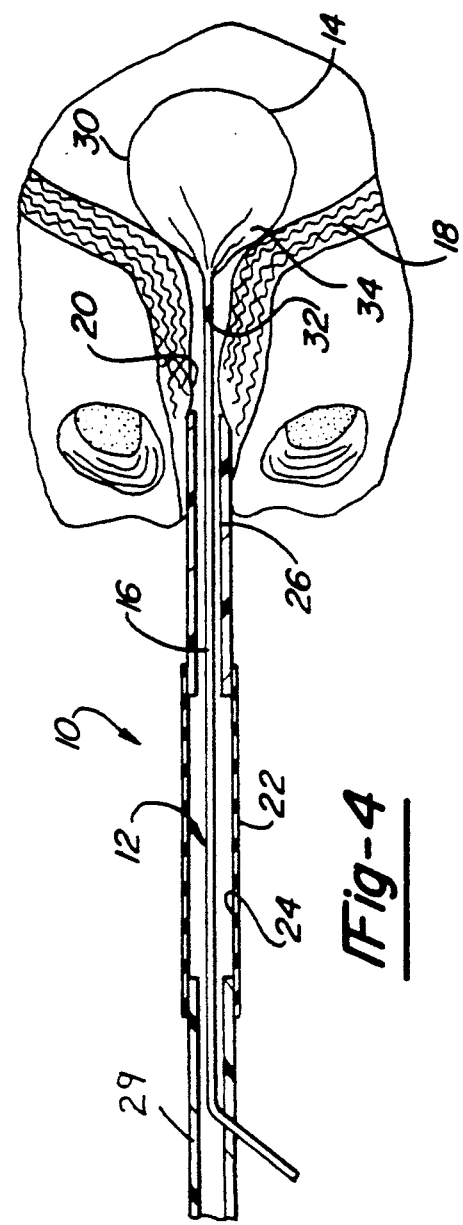
FIG. 4 is a cross sectional view of the present invention as used in catheterizing a female.

More specifically, the intermediate portion 16 has an outer diameter smaller than the inner diameter of the human urethra, as shown in FIGS. 3 and 4, for allowing the flow of urine therebetween. Thusly, as shown in FIGS. 3 and 4, upon catheterization of either the male, as shown in FIG. 3 or the female, as shown in FIG. 4, urine flow is allowed from the bladder 18 over the intermediate portion 16 and within the urethra 20 thereby cleansing the urethra and preventing infection. As shown in the Figures, due to the shorter female urethra, the intermediate portion will be shorter on the female catheter.

The collection means includes a second tubular member 22 disposed over a portion of the intermediate portion 16 and spaced radially therefrom defining a fluid passageway 24. The second tubular member 22 includes a collection plug end portion 26 for insertion into the ostium of the urethra 20, as shown in FIGS. 3 and 4, for preventing urine from escaping from the catheter assembly 10 and collecting the flowing urine into the fluid passageway 24. The fluid passageway 24 will then lead to a collection vessel, not shown. In other words, the smaller diameter intermediate portion 16 allows flow of urine from the bladder 18 through the urethra 20 over the outer surface of the intermediate portion 16. The flow of urine is collected by the collection tube 26. The urine then flows through the fluid passageway 24 into a collection vessel. The collection tube 26 would be inserted at the ostium of the urethra to a sufficient depth, so as to prevent urine from escaping from the drainage system by directing the urine to the collection bag.

A plurality of flexible circular sheds or flanges 27 extend radially outwardly from the collection tube 26. The flanges 27 are either molded with or adhered onto the outer surface of the tube 26.

Figure 11A:
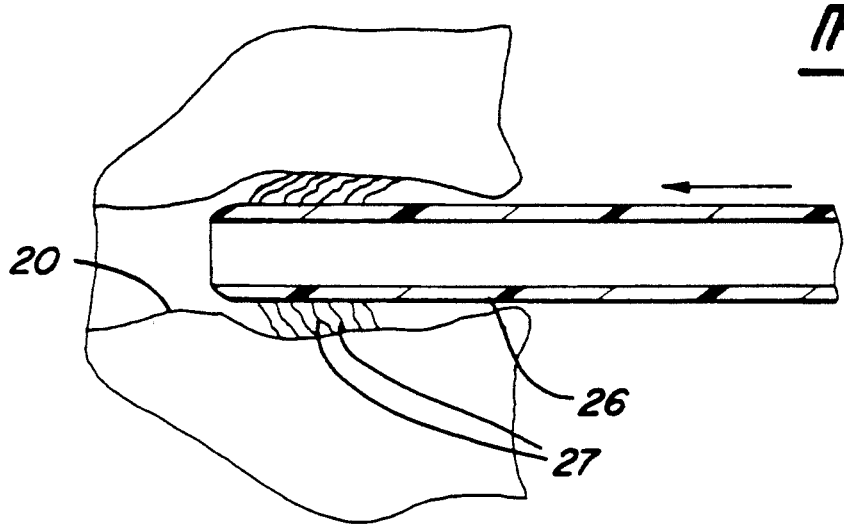
FIGS. 11A and B are enlarged fragmentary cross sectional views of the invention being inserted into the ostium of the urethra.
Figure 11B:
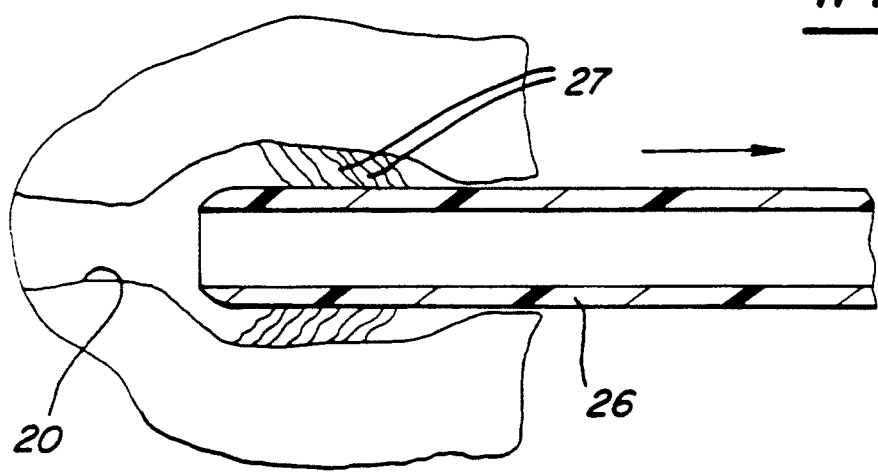

As shown in FIGS. 11A and 11B, as the plug tube 26 is inserted into the ostium of the urethra 20, the flanges 27 will lay against the surface of the collection tube 26 in a distal direction. The tube 26 is purposely inserted into the urethra 20 or approximately one half inch further than required to a sufficient depth to seat the catheter tip into the bladder and then retracted one half inch, as shown in FIG. 11B. The act of retracting the collection tube 26 causes the flanges 27 to reverse their position point in a proximal direction. With the flanges 27 pointing in a proximal direction, the distally directed urine flow tends to open the flexible flanges 27 and causes a seal between the urethra 20 and the flanges 27 in a manner similar to washers having U-shaped cross sections. Thusly, the flanges 27 perfect a seal preventing the fluid collection mechanism of the plug member 26 from leaking between the urethra 20 and the flanges 27.

As shown in FIGS. 1 and 2, the second tube member 22 includes a longitudinally collapsible portion 28 for allowing sliding movement of the plug tube 26 over the intermediate portion 16 without requiring sliding movement of the distal section 29 of the second tubular member 22. The distal section 29 is spaced from the plug tube 26 with the collapsible portion 28 interposed in the gap between the portions 22 and 29 and sealingly attached to both portions 22 and 29. This is illustrated in FIGS. 1 and 2. As shown in FIG. 3, the flexible collapsible portion 28 allows portion 29 to be bent off axis or flexed with respect to portion 26. In FIG. 1, the collapsible portion 28 is shown extended. Once catheterization is accomplished and a specific period of time elapsed, the plug tube 26 can be removed from the ostium of the urethra by sliding movement along the intermediate portion 16 as the collapsible portion 28 collapses, as shown in FIG. 2. Thusly, no further movement of the remainder of the tubular portion 22 is required. The present invention thereby provides a means of periodically removing the collection tube 26 and, by sterile techniques, cleaning the surfaces of the collection tube 26 which comes into contact with the meatus and the distal end of the urethra.

The collection means 22 may be used to collect urine from incontinent patients without the added intermediate tube 16 and balloon 30. The use of the collection tube alone for intermittant catherization or self-catherization greatly simplifies the procedure and dramatically reduces the associated irritation and pain.

On both the male and female patients the collection device may be held in place with a sanitary napkin type retention device.

The longitudinally collapsible portion 28 allows the collection tube 26 to move freely relative to the second tubular portion 22 as well as relative to the intermediate portion 16. Therefore, as the length of the male penis changes or there is movement by either the male or female patient which changes the effective length of the path between the ostium of the urethra 20 and the bladder 18, the plug tube 26 will move freely relative to the intermediate portion 16 and the tip of the catheter 14 which is anchored by the bladder. Thusly, the catheter assembly 10 functions equally well in the male or female patient because the plug tube 26 is free to move and can be adjusted to any length urethra or any changes in length of the urethra.

The intermediate portion 16 includes an inflatable portion 30 adjacent the end portion 14 of the first tubular body portion 12. The inflatable portion 30 defines the retaining means of the present invention. The conventional or Foley retaining balloon utilizes as a collection means a tube protruding proximally from the balloon and is similar to the balloon shown in FIG. 9. It is believed that when this protruding collection means remains in the bladder for a prolonged period, irritation, occurs which precipitates bladder problems. The intermediate portion 16 is a hollow tubular portion and includes a second fluid passageway 32 extending therethrough in fluid communication with the inflatable portion 30 for allowing the passage of fluid therethrough for inflation of the inflatable portion 30. In other words, the intermediate portion also functions as a fluid conduit for directing fluid to inflate or deflate the inflatable portion 30.

As shown in FIGS. 1, 5 and 7, the intermediate portion 16 as well as the portion of the inflatable portion 30 directly adjacent thereto includes opening means for retaining the sphincter adjacent the bladder 18 open for allowing urine flow from the bladder through the urethra and allowing the flow of urine between the inflatable portion 30 and the bladder wall, sphincter opening, and bladder opening to the urethra 20. More specifically, the opening means includes a plurality of pleats 34 on the inflatable portion 30 adjacent the intermediate portion 16 and extending into the intermediate portion 16. The pleats extend parallel relative to the extending length of the first tubular body portion 12. The pleats 34 form ribs extending radially outwardly from the inflatable portion 30 adjacent to the intermediate portion 16 when the inflatable portion is inflated. The ribs define fluid flow channels therebetween which allow the free flow of urine from the bladder therethrough and into the urethra and allow the bladder to empty completely pursuant to the present invention. This pleated end balloon construction prevents bladder perforation and reduces bladder irritation and may also reduce the incidence of squalous carcinoma, pyelonephritis cystitis, bacteremia, and urinary stones as compared to conventional constructions. The rib portions provide a means of holding the sphincter muscle open to allow urine to flow from the bladder and at the same time allows the flow of urine from the bladder to cleanse the area between the balloon and the bladder wall, sphincter muscle, and the bladder opening to the urethra as discussed above. With the fully balloon type retainer as shown in FIG. 9, the grooves 45 provide the same function as the ribs 36 provide in the pleated retainer balloon.

The catheter assembly 10 can be more effective in preventing bladder infection if the urine flow rigorously washes the urethra 20. In a normally functioning urinary system, the bladder sphincter is held closed until the urge to urinate dictates to the person to release the sphincter muscle. The urine is then released and the muscle contractions around the bladder 18 force the urine through the urethra 20 under pressure causing rigorous washing of the urethra 20 to take place. Therefore, it may be desirable to block the flow of urine until a sufficient quantity has accumulated in the bladder 18 to enable the rigorous washing action to take place. Even with patients who have a neurogenic bladder, the build-up of urine and period release will increase the urine flow rate and substantially decrease the incidence of bladder sepsis. This periodic release can be accomplished with either a manual or a time activated valve which closes to retain the urine in the bladder and opens to release the urine. As shown in FIG. 9, the valve can take a form of a valve balloon 52 disposed within the third fluid passageway 40 for selectively blocking the flow of fluid therethrough and selectively opening the previously blocked flow of fluid to enable a rigorous washing action along the length of the intermediate portion 16 by the built-up amount of fluid. The inflatable balloon 52 is disposed within the third passageway 40 and is operatively connected to a fluid supply by lumin 54 which tracks along the intermediate portion 16, as shown in FIG. 10. Alternatively, the valve can be located externally so as to constrict about the end portion 14" of the catheter 10" so as to close off the third inner passageway 40. Of course, other valving configurations can be derived for the various other embodiments of the present invention or may not be required where normal flow from the bladder suffices to prevent migration of bacteria.

The intermediate portion 16 may include second opening means for opening a constricted portion of the urethra and allowing flow of urine therethrough over the intermediate portion 16. More specifically, the second opening means includes a second plurality of ribs 36 shown in detail in FIGS. 7 and 8. The ribs 36 extend radially outwardly from the intermediate portion 16 and parallel relative to the length thereof. The ribs define a second fluid flow channel therebetween. This grooved outside diameter 45 is designed to allow urine to flow through a damaged or traumatized urethra which may have restricted flow due to a swollen prostate, urethral scare tissue or other strictures. The grooved outside diameter supports and maintains an open urethra with the longitudinal peaks and allows the urine to flow through the longitudinal valleys thereof. Again, the free flow of urine prevents infection as set forth above.

As shown in FIGS. 9 and 10, the end portion 14" can include an opening 38 extending therethrough and a third fluid passageway 40 in fluid communication therewith. The third fluid passageway 40 extends through the inflatable portion 30". The third fluid passageway 40 includes an opening 42 about the outer periphery of the intermediate portion 16 for allowing the free flow of urine from the bladder 18 through the inflatable portion 30" and out over the intermediate portion 16. As shown in FIG. 10, passageway 43 is in fluid communication with the inflatable portion 30" for filling and emptying thereof with fluid, to inflate and deflate the portion respectively. The passageway 43 would be in fluid communication with a fluid source (not shown). Thusly, the present invention could be equipped with the pleated end balloon construction or the conventional catheter tip with the balloon inward from the tip and the drainage ports.

The present invention further provides a method of catheterizing a patient for collecting fluid into a drainage system, generally including the steps of inserting the tubular body portion 12 having the portion 14 and the intermediate portion 16 adjacent thereto into urethra 18 of a patient. The intermediate portion 16 is retained in the urethra, as by the inflatable balloon as discussed above. The free flow of urine is allowed to flow from the bladder 18 and over the intermediate portion 16 of the catheter thereby maintaining an infection free bladder and urethra. The urine flowing over the intermediate portion 16 is collected while the escape of the urine from the drainage system is prevented.

More specifically, the collection end portion 26 of the second tubular member 22, which is disposed over the intermediate portion 16, is inserted into the ostium of the urethra 22, and collects the free flowing urine flowing over the intermediate portion 16 into the plug end 26 and through the fluid flow channel 24 between the first and second tubular members 12 and 22. Irrigation of the urethra is accomplished by the flow through the center lumen 46 as shown in FIG. 9.

In use, the catheter assembly 10 is inserted by engaging the distal end of the tip 14 with the proximal end of the collection tube 26 and pushing the distal end of the collection tube 26 until the catheter assembly 10 is in place. The collection tube 26 is of sufficient length to allow insertion. The balloon 30, 30',30" is then inflated to anchor the catheter assembly 10 in place. The catheter assembly 10 is removed by deflating the balloon 30 and then removing the collection tube 26 from the ostium of the urethra 20. Lastly, the intermediate portion 16 is pulled on which is attached to the catheter tip 14 until the catheter assembly 10 is completely removed.

In view of the above, the present invention provides means for preventing the multiplying and migrating of bacteria and fungi without the necessity of impregnating the catheter with antimicrobial materials or other means as provided by the prior art. It also provides a means of irrigating the bladder and urethra to further prevent the migrating and multiplying of bacteria and fungi.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims wherein reference numerals are merely for convenience and are not to be in any way limiting, the invention may be practiced otherwise than as specifically described.

What is claimed is:

1. A catheter assembly (10) for collecting urine from a urethra into a drainage system, said catheter assembly (10) comprising: a first tubular body portion (12) having an end portion (14) and an intermediate portion (16) adjacent thereto, said intermediate portion (16) having an outer surface, said end portion (14) including retaining means for retaining said intermediate portion (16) within the urethra, said intermediate portion (16) including flow means for allowing the free flow of urine from the bladder (18) and over the intermediate portion (16) and through the urethra (20) to maintain an infection free bladder (18) and urethra (20); and a second tubular member (22) including a collection end portion (26) operatively connected about and containing a portion of said intermediate portion (16) and spaced from said end portion (14), said collection end portion (26) being insertable at the ostium of the urethra (20) for collecting the fluid flow over said intermediate portion (16) and preventing the fluid from escaping from the draining system, said collection end portion (26) forming a tubular channel for fluid flow between said collection end portion (26) and said outer surface of said intermediate portion (16) contained therein, said second tubular member (22) including a distal portion (29) spaced from said collection end portion (26), and a collapsible portion interposed between said collection end portion (26) and said distal portion (29) for allowing sliding movement of said collection end portion (26) relative to said end portion (14) of said first tubular body portion without relative movement of said first tubular body portion (12) with respect to the distal portion (29) of said second tubular member (22) and flexing of the collapsible portion for allowing said distal portion to bend off axis with respect to the collection end portion (26);

said free flow means for allowing the free flow of urine through said collapsible portion and through said distal portion (29).

2. A catheter as set forth in claim 1 wherein said intermediate portion (16) has an outer diameter smaller than an inner diameter of a human urethra for allowing the flow of urine herebetween, said second tubular member (22) including a plug end portion for insertion into the ostium of the urethra (20) for preventing urine from escaping from said catheter assembly (10) and collecting the flowing urine into said fluid passageway (24).

3. A catheter as set forth in claim 2 wherein said second tubular member (22) includes flexible circular sealing flange means extending radially outwardly therefrom for perfecting a seal against the wall of the urethra (20) to prevent leakage of urine between the urethra (20) and the portion of said second tubular member (22) inserted therein.

4. A catheter as set forth in claim 3 wherein said means includes at least one flexible circular flange extending radially outwardly from said second tubular member (22).

5. A catheter as set forth in claim 1 wherein said intermediate portion (16) includes an inflatable portion (30) adjacent said end portion (14) of said first tubular body portion (12) defining said retaining means, said intermediate portion (16) being hollow and including a second fluid passageway (32) in fluid communication with said inflatable portion (30) for allowing the passage of fluid therethrough for inflation of said inflatable portion (30).

6. A catheter as set forth in claim 5 wherein said intermediate portion (16) includes opening means for retaining the sphincter adjacent the bladder (18) open for allowing urine flow from the bladder through the urethra and allowing flow of urine between said inflatable portion (30) and the bladder wall sphincter opening and bladder opening to the urethra (20).

7. A catheter as set forth in claim 6 wherein said opening means includes a plurality of pleats (34) on said inflatable portion (30) adjacent said intermediate portion (16) and extending parallel relative to the extending length of said first tubular body portion (12), said pleats (34) forming ribs extending radially outwardly from said inflatable portion (30) adjacent to said intermediate portion (16) when said inflatable portion is inflated and defining fluid flow channels therebetween.

8. A catheter as set forth in claim 7 wherein said intermediate portion (16) includes second opening means for opening a constricted portion of the urethra and allowing flow of urine therethrough over said intermediate portion (16).

9. A catheter as set forth in claim 8 wherein said second opening means includes a plurality of second ribs (36) extending radially outwardly from said intermediate portion (16') and parallel relative to the length thereof; said ribs defining second fluid flow channels therebetween.

10. A catheter as set forth in claim 5 wherein said end portion (14") includes an opening (38) therethrough and a third fluid passage (40) in fluid communication therewith, said third fluid passageway (40) extending through said inflatable portion (30"), said third fluid passageway (40) including an opening (42) to said intermediate portion (16) for allowing the free flow of urine from the bladder (18), through said inflatable portion (30"), and out over said intermediate portion (16) for irrigating the bladder and urethra.

11. A catheter as set forth in claim 10 further including valve means with said third fluid passageway (40) for selectively blocking the flow of fluid therethrough and selectively opening the previously blocked flow of fluid to enable a rigorous washing action along the length of said intermediate portion (16) by the built-up amount of the fluid.

12. A catheter as set forth in claim 11 wherein said valve means includes an inflatable balloon (52) disposed within said third passageway (40) and fluid supply lumen (57) operatively connected thereto and disposed within said intermediate portion for connection to a fluid source.

13. A urethra catheter assembly (10) for collecting urine from a urethra into a drainage system, said catheter assembly comprising: a collection tube (26) insertable at the ostium of the urethra for collecting fluid therein and preventing fluid from escaping from said assembly (10) and at least one thin annular flexible circular flange (27) extending radially outwardly from said collection tube (26) and constructed to be resiliently flexible towards and away from said collection tube (26) for perfecting a seal against the wall of the urethra (20) to prevent leakage of fluid between the urethra (20) and the portion of the collection tube (26) inserted therein, said tube (26) slidably receiving a tube member (16) therein that forms a fluid passage (24) therebetween.

14. A method of catheterizing a patient for collecting fluid into a drainage system including the steps of: inserting a collecting tube (26) into the ostium of the urethra, the collecting tube (26) including flexible circular flanges (27) extending radially outwardly therefrom, the flanges (27) laying against an adjacent surface of the collecting tube (26) in a direction away from the patient's bladder (18); retracting the collecting tube (26) sufficiently to force the flanges (27) to reverse the direction of the flange (27) towards the patient's bladder (18), fluid flow in the urethra opening the flanges (27) to perfect a seal between the collecting tube (28) and the urethra (20).

15. A urethra catheter comprising:
 a catheter intermediate member having an outer diameter smaller than an internal diameter of a hydro-dynamically inflated human urethra for allowing urine flow circumferentially about the entire exterior circumference of the catheter intermediate member;
 a retainer at an axial inner end of said catheter intermediate member for retaining said inner end of said intermediate member within a human bladder;
 a tubular collection member mountable at a downstream end of said human urethra having an open axial inner end and a sealing device about an outer diameter to prevent fluid flow about and around said collection member;
 said intermediate member extending through said axial inner end of said collection member and forming an annular channel between said intermediate member and said tubular collection member to provide flow of urine therethrough;
 said tubular collection member having an open distal end to allow urine flow through said annular channel from said human urethra.

16. A urethra catheter as defined in claim 15 further comprising;
 said collection member includes a first axially positioned inner tube and a second axially positioned outer tube spaced from said first tube and a collapsible section therebetween with said collapsible section forming a section of outer wall for said annular channel for urine flow therethrough
 said intermediate portion affixedly mounted to said axially outer tube member and slideable with respect to said axially inner tube member.

* * * * *